(12) United States Patent
Schmotzer et al.

(10) Patent No.: US 6,364,911 B1
(45) Date of Patent: Apr. 2, 2002

(54) FEMORAL SLED PROSTHESIS

(75) Inventors: Hans Schmotzer, Aarau (CH); Peter Schuler; Udo Malzer, both of Karlsruhe (DE)

(73) Assignee: Plus Endoprothetik AG, Rotkreuz (CH)

( * ) Notice: Subject to any disclaimer, the term of this patent is extended or adjusted under 35 U.S.C. 154(b) by 0 days.

(21) Appl. No.: 09/403,645

(22) PCT Filed: Apr. 22, 1998

(86) PCT No.: PCT/EP98/02376

§ 371 Date: Mar. 8, 2000

§ 102(e) Date: Mar. 8, 2000

(87) PCT Pub. No.: WO98/47448

PCT Pub. Date: Oct. 29, 1998

(30) Foreign Application Priority Data

Apr. 22, 1997 (DE) ......................... 197 16 879

(51) Int. Cl.[7] .................................. A61F 2/38
(52) U.S. Cl. .......................... 623/20.31; 623/20.35
(58) Field of Search ..................... 623/20.2, 20.31, 623/20.35, 20.14, 20, 20.21

(56) References Cited

U.S. PATENT DOCUMENTS

| | | | |
|---|---|---|---|
| 3,816,855 A | * | 6/1974 | Saleh ..................... 623/20.31 |
| 4,888,020 A | | 12/1989 | Horber |
| 5,326,361 A | | 7/1994 | Hollister |
| 5,549,688 A | | 8/1996 | Ries, et al. |
| 5,609,643 A | * | 3/1997 | Colleran et al. ......... 623/20.29 |

FOREIGN PATENT DOCUMENTS

| | | |
|---|---|---|
| DE | 34 44 001 | 12/1986 |
| DE | 40 41 920 | 6/1994 |
| DE | 44 35 286 | 10/1996 |
| EP | 0 551 791 | 7/1993 |
| WO | WO 87/02882 | 5/1987 |
| WO | WO 93/05729 | 4/1993 |
| WO | WO 96/03939 | 2/1996 |

* cited by examiner

Primary Examiner—Bruce Snow
Assistant Examiner—Brian E. Pellegrino
(74) Attorney, Agent, or Firm—Knobbe, Martens, Olson & Bear, LLP

(57) ABSTRACT

A femur slide has a patella shield and two convex curved condyle cups which are anteriorly rigidly joined by the patella shield. The two condyle cups and the patella shield define internally anterior and posterior matching surfaces which correspond with a femural ventral cut and with a femural dorsal cut. Relative to a reference plane which is defined by posterior slide surfaces of the condyle cups, an anterio-medial matching surface lies nearer to the reference plane than an anterio-lateral matching surface. The anterior matching surfaces are defined by a slanted surface with is continuously slanted in a direction from lateral to medial to posterior, and an angle between the slanted surface and the reference plane lies between three and ten degrees.

21 Claims, 3 Drawing Sheets

FEMORAL SLED PROSTHESIS

FIELD OF THE INVENTION

The invention relates to a femur slide comprising two convex curved condyle cups which are anteriorly rigidly joined by a patella shield.

BACKGROUND OF THE INVENTION

Femur slides of this type are generally known. In this respect, reference is made, for example, to DE 40 41 920 C2 or WO 87/02882.

In present day operation techniques for knee-joint replacement on the femur, the implant is aligned at the rear or posterior condyles. An equal amount of bone is removed from both condyles. The anterior or central cut lies parallel to the posterior or dorsal cut and thus to the posterior condyle edge. However, this has a disadvantage for various technical and anatomical reasons in that firstly the rotational axis no longer coincides with the axis offered by the side bands and secondly the implant is, due to the non-anatomical position in the curvature, seated either too tightly on the medial side or too loosely on the lateral side.

For this reason, experts in knee-joint endoprosthetics recommend an outward rotation for the condyles. The orientation is served either by the so-called epicondyle axis or the so-called "whiteside" line. Due to this outside rotation of the cutting instruction, laterally less bone relative to the medial side is removed in the posterior area. At the same time, more bone is resected anterio-laterally as compared to the medial side. However, as the implants are matched to the original cutting line which is characterized by equal material thickness medially and laterally, a higher buildup results on the lateral side which compensates the undesirable play on the lateral side in the curvature. At the same time, the outside rotation of the implant laterally offsets the patella socket which reduces the danger of patella subluxations. However, this process presents the following disadvantages:

The anterio-lateral edge of the implant often protrudes over the bone edge;

due to lower cut orientation on the lateral side, the anterior cortex is often cut into which is undesirable for various reasons;

the patella shield of the implant protrudes on the medial side over the bone, i.e. a gap remains between shield and bone. The reason for this lies in the natural geometry of the anterior femur which is medially slanted in the distal area.

SUMMARY OF THE INVENTION

It is an object of the present invention to make available a femur slide by means of which advantages of the conventional cuts at the distal end of the femur can be maintained, in which in particular the saw cuts can be better matched to the anatomy of the femur whilst at the same time achieving a kinematically optimal position of the implant with outside rotation.

An object of the invention involves a femur slide having a patella shield and two convex curved condyle cups which are anteriorly rigidly joined by the patella shield. The two condyle cups and the patella shield define internally anterior and posterior matching surfaces which correspond with a femural ventral cut and with a femural dorsal cut. Relative to a reference plane which is defined by posterior slide surfaces of the condyle cups, an anterio-medial matching surface lies nearer to the reference plane than an anterio-lateral matching surface. The anterior matching surfaces are defined by a slanted surface with is continuously slanted in a direction from lateral to medial to posterior, and an angle between the slanted surface and the reference plane lies between three and ten degrees.

Thus, the basic idea of the present invention lies in rotating the anterior or ventral cut in the transversal plane. In a preferred arrangement, the dorsal cut remains parallel to the condyles or parallel to the plane defined by the posterior slide surfaces of the condyle cups. In particular the thickness of the dorsal condyle cups shall be medially and laterally equal in a further preferred arrangement.

The inventive structure achieves anatomical matching, and it is left to the surgeon to position the precise amount of rotation intraoperatively and in dependence of the individual anatomy.

BRIEF DESCRIPTION OF THE DRAWINGS

A form of embodiment of a femur slide configured according to the invention will now be described in more detail, based on the enclosed drawing. Shown are in FIG. 1: a femur slide according to the invention, in a perspective view from an angle at the top.

DETAILED DESCRIPTION OF THE INVENTION

Figure 1:
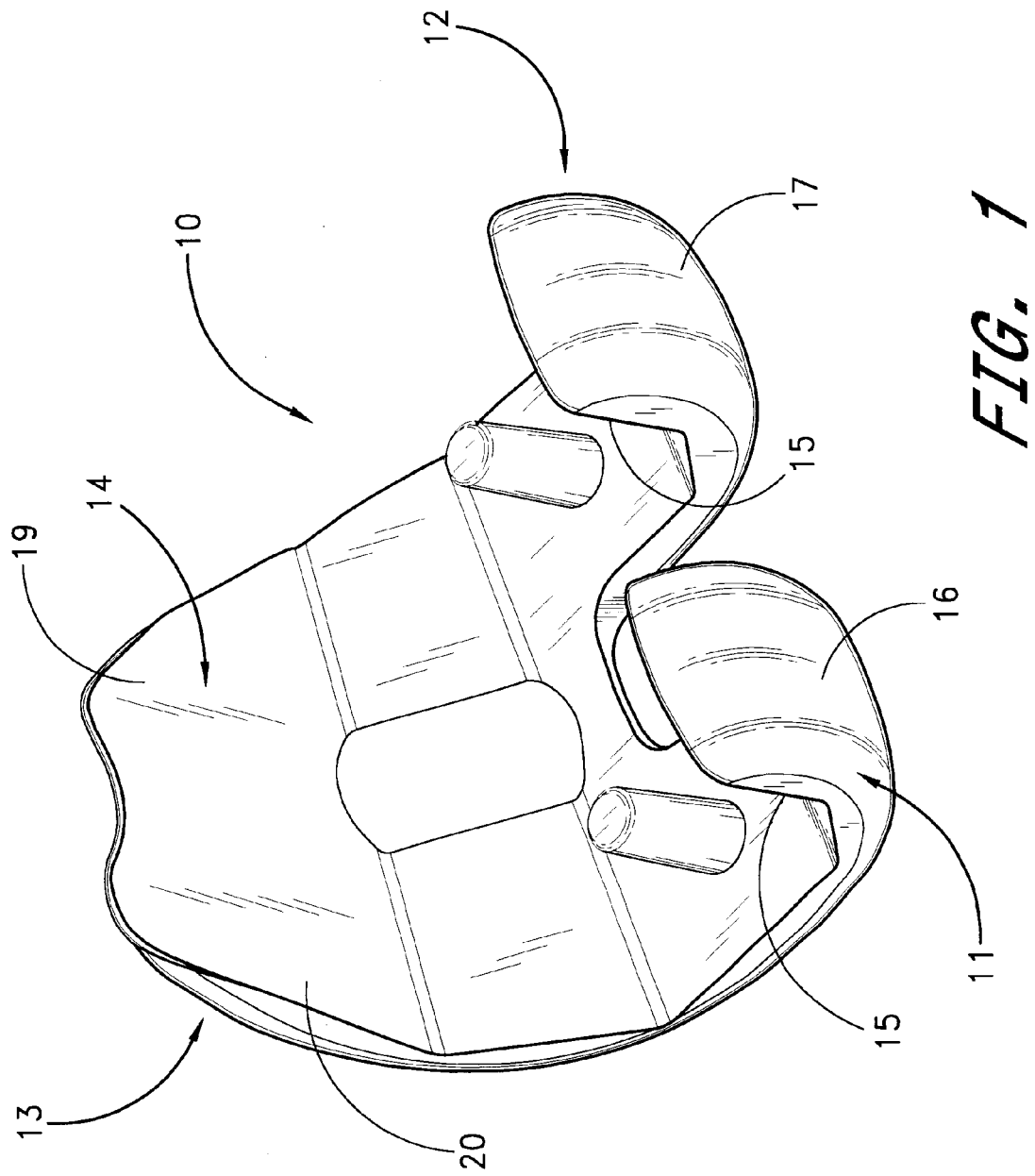
Figure 2:
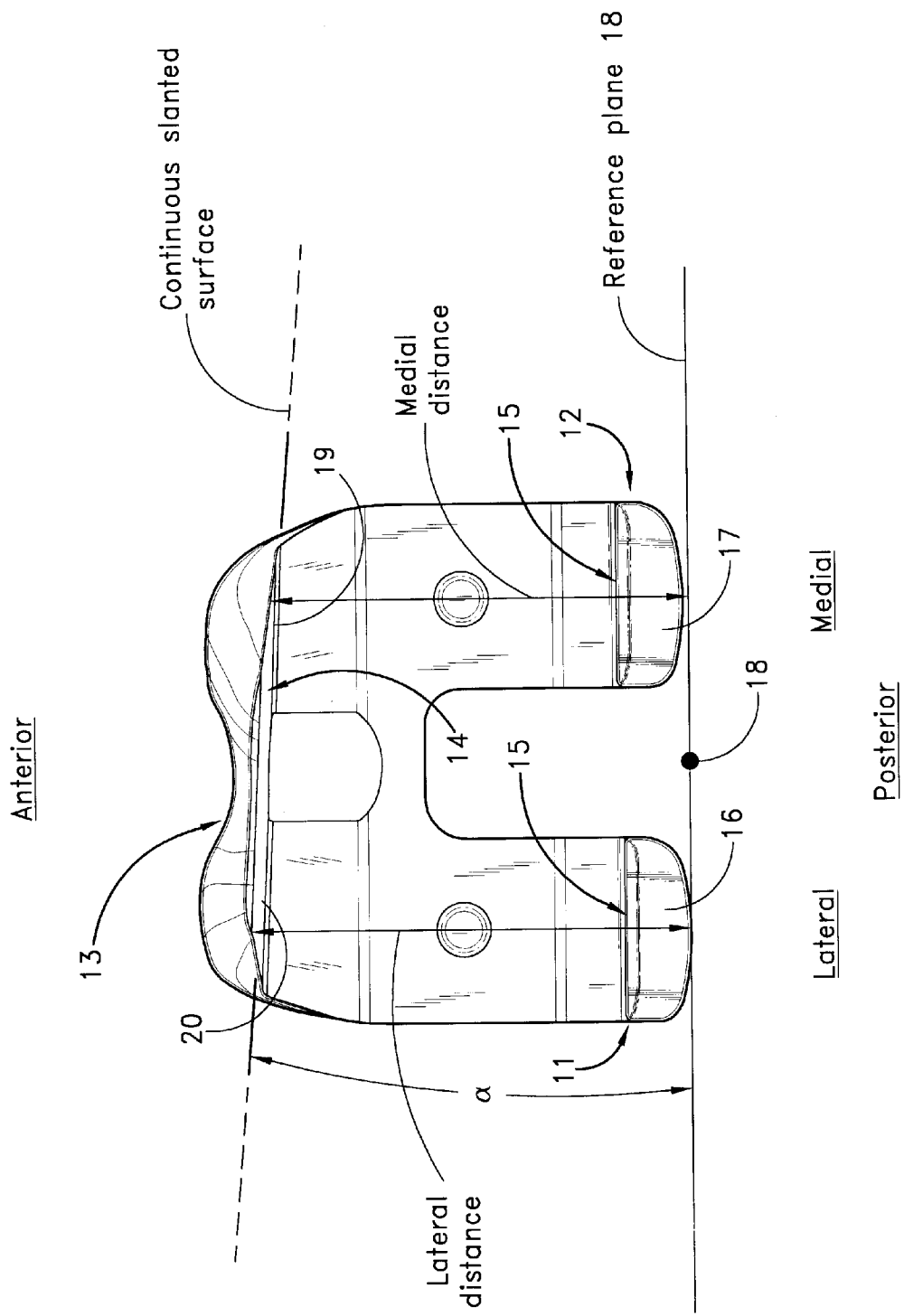
FIG. 2: the femur slide as in FIG. 1, in a top view. i.e. from superior.
Figure 4:
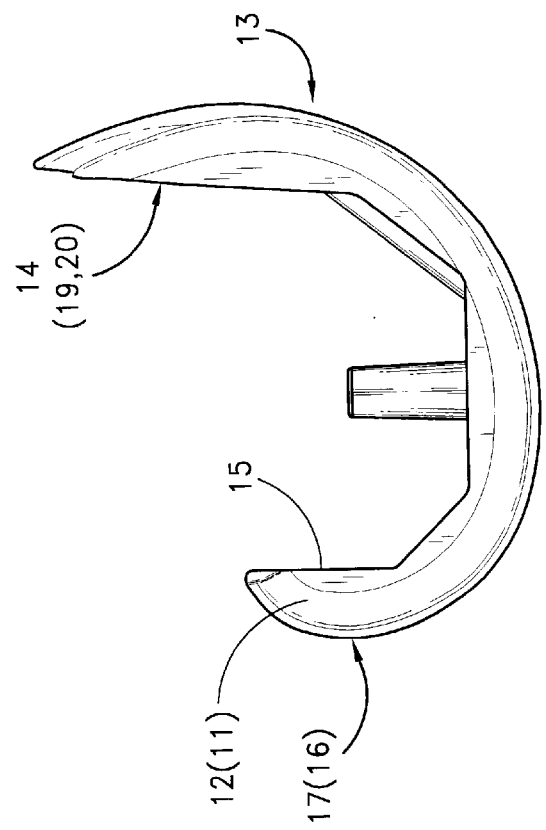
FIG. 4: the femur slide as in the above figures, in a side view, i.e. in a view from medial.
Figure 3:
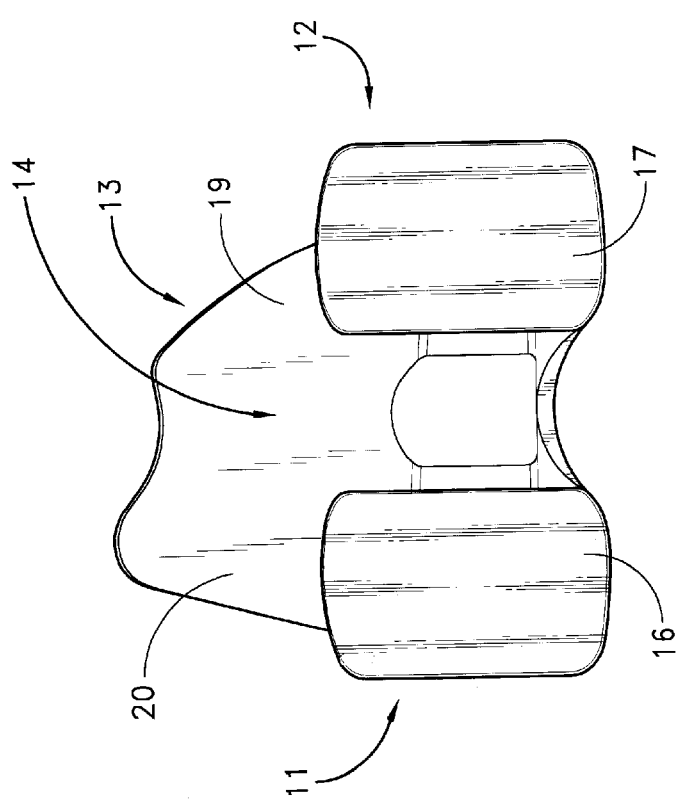
FIG. 3: the femur slide as in FIGS. 1 and 2, in a view from the rear or posterior.

In FIG. 1 is illustrated a femur slide 10 which is characterized by two convex curved condyle cups 11, 12 as well as a patella shield 13. Both condyle cups 11, 12 are rigidly joined together by patella shield 13. To this extent, this is a conventional structure of a femur slide. Both condyle cups 11, 12 and patella shield 13 define internally anterior and posterior matching surfaces 14, 15 (also see FIG. 2) which correspond with a femural ventral cut on the one hand and a femural dorsal cut on the other hand. These matching surfaces are associated with the ventral and dorsal saw-cut surface at the distal end of the femur.

The posterior slide surfaces of condyle cups 11, 12, which are designed like sliding skids, are denoted 16 and 17. According to FIG. 2, posterior slide surfaces 16, 17 of condyle cups 11, 12 define a reference plane 18. With respect to this reference plane 18, the anterio-medial matching surface 19 lies closer to this reference plane 18 than anterio-lateral matching surface 20. In a concrete case, anterior matching surfaces 19, 20 are defined by a continuous slanted surface which is slanted in the direction from lateral to medial to posterior, and the angle α between this and reference plane 18 lies between 3 and 10 degrees, in particular approximately 5 to 7 degrees. In the concrete form of embodiment as in FIGS. 1 to 4, the anterio-medial and anterio-lateral matching surfaces 19, 20 are combined into one common anterior matching surface 19.

However, it is also feasible that the anterio-lateral matching surface 20 extends relative to reference surface 18 at a different angle, in particular a more flat angle, than anterio-medial matching surface 19.

It is also feasible that the anterio-lateral and anterio-medial matching surface extends approximately parallel to each other, in particular also parallel to reference plane 18.

The aforementioned forms of embodiment are patient-dependent. However, all of them distinguish themselves by the aforementioned objective.

The connecting surface between the anterio-lateral and anterio-medial matching surface can be designed to be continuously plane or alternatively curved or bulged. In the illustrated form of embodiment, this is a plane surface which integrally merges into both matching surfaces 19, 20.

The posterio-lateral and posterio-medial matching surfaces 15 extend in the illustrated form of embodiment parallel to reference plane 18, and the distance to reference plane 18 is always the same.

It is also feasible that the distance of the two posterior matching surfaces 15 differs from reference plane 18. Furthermore, it is feasible that these matching surfaces extend at an angle, i.e. either a common or a different angle relative to the reference plane. Finally, it is also feasible that posterior matching surfaces 15 extend parallel to the anterior matching surfaces.

All features revealed in the application documents are claimed as essential parts of the invention inasmuch as they are individually or in combination new relative to the prior art.

List of Reference Numbers

10 Femur Slide
11 Condyle Cup
12 Condyle Cup
13 Patella Shield
14 Anterior Matching Surface
15 Posterior Matching Surface
16 Posterior Slide Surface
17 Posterior Slide Surface
18 Reference Plane
19 Anterio-Medial Matching Surface
20 Anterio-Lateral Matching Surface
α Angle between Anterior Matching Surfaces and Reference Plane.

What is claimed is:

1. A femur slide, comprising:
   a patella shield; and
   two convex curved condyle cups which are anteriorly rigidly joined by the patella shield, wherein the two condyle cups and the patella shield define internally anterior and posterior matching, surfaces which correspond with a femural ventral cut and with a femural dorsal cut, and wherein, relative to a reference plane which is defined by posterior slide surfaces of the condyle cups, an anterio-medial matching surface lies nearer to the reference plane than an anterio-lateral matching surface, wherein the anterior matching surfaces are defined by a slanted surface with is continuously slanted in a direction from lateral to medial to posterior, and an angle α between the slanted surface and the reference plane is between about three and ten degrees.

2. The femur slide according to claim 1, wherein the angle α is between about five and seven degrees.

3. The femur slide according to claim 2, wherein a connecting surface between the anterio-lateral and the anterio-medial matching surface is one of a continuous plane or a curved transitional surface.

4. The femur slide according to claim 1, wherein the anterio-lateral matching surface extends relative to the reference plane at a different angle than the anterio-medial matching surface extends relative to the reference plane.

5. The femur slide according to claim 1, wherein the anterio-lateral matching surface extends relative to the reference plane at a more flat angle than the anterio-medial matching surface.

6. The femur slide according to claim 1, wherein the posterior-lateral matching surface and the posterior-medial matching surface extend parallel to each other.

7. The femur slide according to claim 1, wherein the posterior-lateral matching surface and the posterior-medial matching surface extend parallel to each other and parallel to the reference plane.

8. The femur slide according to claim 1, wherein the posterior-lateral matching surface and the posterior-medial matching surface extend at an angle relative to the reference plane.

9. The femur slide according to claim 1, wherein the posterior-lateral matching surface and the posterior-medial matching surface extend relative to the reference plane in parallel.

10. The femur slide according to claim 1, wherein the posterior-lateral matching surface and the posterior-medial matching surface extend relative to the reference plane at an angle corresponding with a slant of the anterior matching surfaces.

11. The femur slide according to claim 1, wherein the posterior matching surfaces are laterally and medially at the same distance from the reference plane.

12. The femur slide according to claim 1, wherein the posterior matching surfaces are laterally and medially at a different distance from the reference plane.

13. A femur slide, comprising:
    a patella shield; and
    two convex curved condyle cups which are anteriorly rigidly joined by the patella shield, wherein the two condyle cups and the patella shield internally define anterior and posterior matching surfaces which correspond with a femural ventral cut and with a femural dorsal cut, and wherein, relative to a reference plane as defined by posterior slide surfaces of the condyle cups, an anterior-medial matching surface of this reference plane lies closer than an anterior-lateral matching surface, wherein the anterior-lateral and anterior-medial matching surfaces extend parallel to each other.

14. The femur slide according to claim 13, wherein the anterior-lateral and anterior-medial matching surfaces extend parallel to each other arid parallel to the reference plane.

15. The femur slide according to claim 14, wherein a connecting surface between the anterio-lateral and the anterio-medial matching surface is one of a continuous plane or curved transitional surface.

16. The femur slide according to claim 13, wherein the posterior-lateral matching surface and the posterior-medial matching surface extend parallel relative to the reference plane.

17. The femur slide according to claim 13, wherein the posterior-lateral matching surface and the poskerior-medial matching surface extend at an angle relative to the reference plane.

18. The femur slide according to claim 13, wherein the posterior-lateral matching surface and the posterior-medial matching surface extend relative to the reference plane in parallel.

19. The femur slide according to claim 13, wherein the posterior-lateral matching surface and the posterior-medial matching surface extend relative to the reference plane at an angle corresponding with a slant of the anterior matching surfaces.

20. The femur slide according to claim 13, wherein the posterior matching surfaces are laterally and medially at the same distance from the reference plane.

21. The femur slide according to claim 13, wherein the posterior matching surfaces are laterally and medially at a different distance from the reference plane.

* * * * *

UNITED STATES PATENT AND TRADEMARK OFFICE
CERTIFICATE OF CORRECTION

PATENT NO.    : 6,364,911 B1
DATED         : April 2, 2002
INVENTOR(S)   : Schmotzer et al.

It is certified that error appears in the above-identified patent and that said Letters Patent is hereby corrected as shown below:

<u>Column 4,</u>
Line 49, please change "poskerior medial" to -- posterior medial --.

Signed and Sealed this

Twentieth Day of August, 2002

Attest:

Attesting Officer

JAMES E. ROGAN
*Director of the United States Patent and Trademark Office*